United States Patent [19]

Wood

[11] Patent Number: Plant 7,680

[45] Date of Patent: Oct. 15, 1991

[54] *FICUS BENJAMINA* 'CITATION'

[76] Inventor: Bret T. Wood, 27999 Lake Jem Rd., Mt. Dora, Fla. 32745

[21] Appl. No.: 520,352

[22] Filed: May 7, 1990

[51] Int. Cl.[5] ..... A01H 5/00

[52] U.S. Cl. ..... Plt./88

[58] Field of Search ..... Plt./88, 33, 51, 54

*Primary Examiner*—James R. Feyrer

*Attorney, Agent, or Firm*—Frank B. Robb

[57] ABSTRACT

A sport of *Ficus benjamina* Exotica, presenting tightly or deeply curled foliage which in cross-section is V-shaped in contrast to the usual flat leaves of the known *Ficus benjamina,* the overall appearance of a bush of my new variety showing a general aspect of rather tightly curled appearance and thus denser whether as bush, shrub, pillar or standard tree form.

2 Drawing Sheets

BACKGROUND OF THE DISCLOSURE

As the operator of a plant nursery which grows and sells large quantities of many different plant varieties, foliage plants being among them, I am constantly observing the plants during growth, to ascertain if there are unusual appearance or other aspects which would offer potential for sales and attractiveness not currently available.

Thus, this would create and sustain new markets for plant products which can be grown in the nursery with which I am connected.

Since the nursery is in the vicinity of Lake Jem, Fla., generally central in the state, I have been instrumental in growing and selling Ficus of many varieties, particularly the *F. benjamina.*

During growth of such *F. benjamina* which by pruning and appropriate training can take several forms, it is desirable to provide the trade with all forms and sizes, some of which are more appealing in one form than another.

As a result of the foregoing I observed the sport of the *F. benjamina* grown in the nursery and the peculiar curly aspect of its leaves, caused me to grow plants from cuttings of the sport.

This led to causing my new plant to be asexually reproduced by cuttings and tissue culture with the ultimate growing of the same in all the usual forms and establishing that the curly form of the leaves was a continuing characteristic which over time came true in successive generations and thus resulted in a plant of substantially different appearance from the usual *Ficus benjamina.*

SPECIFIC DESCRIPTION OF THE PLANT

My new plant is adaptable for use and growth in the areas where *F. benjamina* is and has been grown. It is particularly notable that a much denser appearance of my new plant is presented when compared with the usual *F. benjamina* grown and shaped in a substantially identical form, and my new plant is illustrated in the drawing appended hereto, in FIG. 1 as a pillar type plant, just one form and suggests the curly overall appearance of the leaves thereof.

FIG. 2 is a close up view of some of the leaves of my new plant clearly disclosing the V-shaped cross-section of the leaves and the tightly curled nature thereof:

A somewhat generalized description of my new variety could include the following wherein I deal with some of the specific aspects of the plant.

Under the same growing conditions as *Ficus benjamina* Exotica, i.e. coming from the same shadehouse area in which light (60 percent saran shadecloth), temperature (range 40 degrees fahrenheit to 95 degrees fahrenheit), water (overhead irrigation), fertilizer (18-6-12 osmocote), soil mix (60 percent native Florida peat, 40 percent sawdust, 10 percent sand), pot size (7 gallon), plant height (approximately 6 feet) and of untrained, multi-plant bush form, the following observations are stated:

1. Stiffness is the same.
2. No noticeable difference in internode length and leaf count and thus no apparent difference in compactness.
3. No noticeable difference in caliper size or stoutness of limb.
4. No difference in actual leaf thickness.

The untrained habit as shown in FIG. 1 is denser in appearance only. The unique leaf shape is the major contributor to the denser appearance.

The mature bark color is as stated and appears to be closely identical to that of the parent, under the same growing conditions. This description is based on observing plants which are shade grown, contributing to the light olive color as compared to that of sun grown plants which are near white in color.

There does not appear to be any noticeable difference in plant height or vigor between the parent and my new plant of the same age.

As a basis for commercial sale of my new variety I have selected the designation "Citation" for my new plant and believe it will find acceptance under that name in the trade.

Under the growing conditions as previously stated the following measurements are representative:

| | Ficus Benjamina | Ficus Citation |
|---|---|---|
| Mature Leaf Width | $\frac{5}{8}$" to $1\frac{3}{8}$" | 1 1/16" to $1\frac{3}{8}$" |
| Mature Leaf Length | $1\frac{3}{4}$" to 3" | $1\frac{1}{2}$" to $2\frac{3}{8}$"/curled<br>$1\frac{3}{4}$" to $2\frac{3}{4}$"/uncurled |
| Number of leaves Per foot | 42–49 | 44–48 |

My new plant has not fruited.

In the detailed description which follows, I have related the color notations to those of the Munsell Color Fan and further believe the colors shown are as closely related to those of the plant as is possible to obtain in photographic reproductions of the nature herein provided.

It thus appears that the most outstanding difference between the parent plant and plants of my new variety resides in the curled and slightly shorter leaf caused by the curl in tha leaf of my new variety.

DETAILED DESCRIPTION

Figure 1:
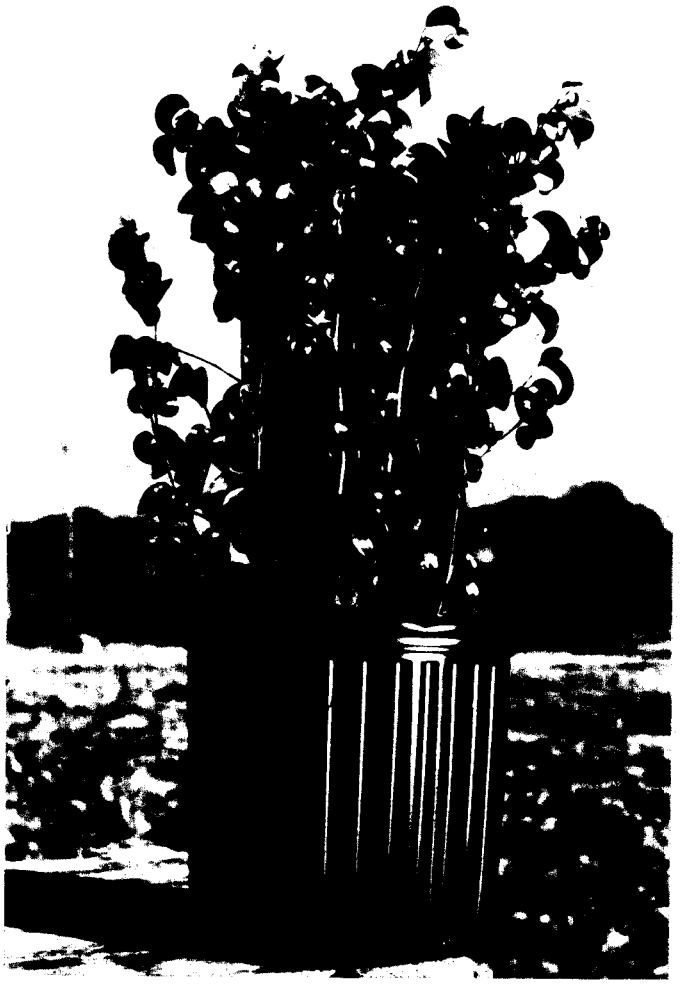
Figure 2:
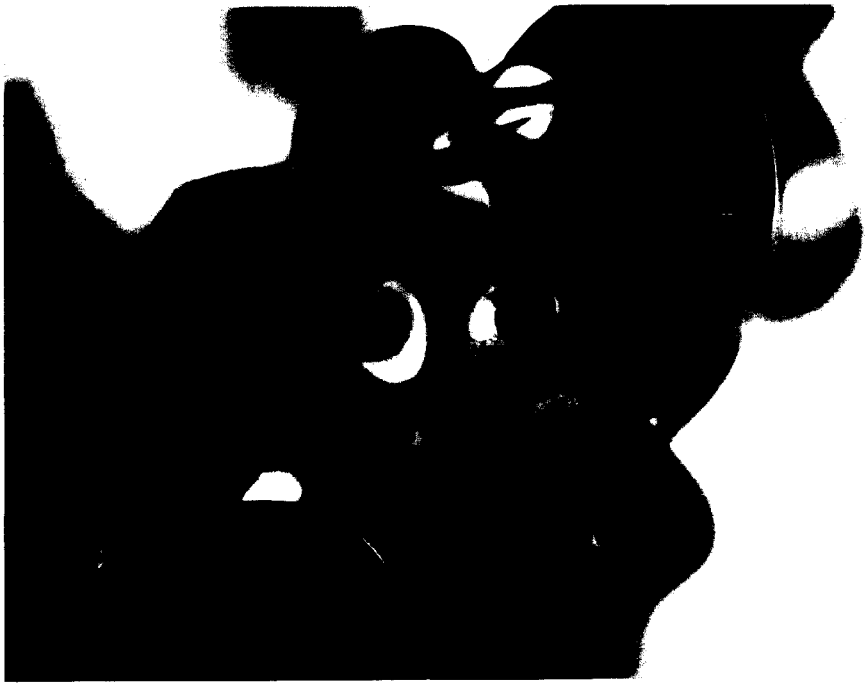

Plant:

*Form.*—Bush; shrub; pillar; standard tree; braid.
*Growth.*—Vigorous; uprights; branching.
*Height.*—2 inches to 50 feet, not limited by form.
*Spread.*—Not limited by form.

Foliage:

*Leaflets.*—1.
*Size.*—Medium.
*Quantity.*—Normal.
*New color.*—Upper side; 5GY 7/10 Strong yellow green. Under side: 5GY 7/10 Strong yellow green.
*Mature color.*—Upper: 5GY 4/3 Moderate olive green. Under: 5GY 5/6 Moderate yellow green.

*Shape.*—Oval pointed; curled under.
*Texture.*—Glossy.
*Ribs and veins.*—Ordinary.
*Edge.*—Smooth.
*Leaf stem.*—Color: 5GY 5/6 Moderate yellow green.
*Under side.*—Smooth.
*Stipules.*—Short; smooth.

Disease resistance: Resistant.

Wood (new):

*Color.*—2.5Y 4/4 Moderate olive brown.
*Bark.*—Smooth.

Wood (old):

*Color.*—7.5Y 5/5 Light olive.
*Bark.*—Smooth.

I claim:

1. A new and distinct variety of *Ficus benjamina* plant substantially as herein shown and described, characterized particularly as to novelty by the tightly curled form of its leaves, which are deeply V-shaped in cross-section, presenting a dense overall plant appearance as bush, shrub, pillar and standard tree form, the other characteristics of my new variety being essentially the same as those of *F. benjamina.*

* * * * *